United States Patent
Battenberg et al.

(10) Patent No.: US 6,247,353 B1
(45) Date of Patent: Jun. 19, 2001

(54) DIGITAL ULTRASONIC MONITORING SYSTEM AND METHOD

(75) Inventors: Rexford A. Battenberg; Terry G. Carpenter; William S. Johnson; Kenneth R. Piety; Kenneth C. Puterbaugh; James C. Robinson, all of Knoxville; James B. Vanvoorhis, Kingston, all of TN (US)

(73) Assignee: CSI Technology, Inc., Wilmington, DE (US)

( * ) Notice: Subject to any disclaimer, the term of this patent is extended or adjusted under 35 U.S.C. 154(b) by 0 days.

(21) Appl. No.: 09/458,293

(22) Filed: Dec. 10, 1999

Related U.S. Application Data

(63) Continuation of application No. 09/075,560, filed on May 4, 1998, now abandoned.

(51) Int. Cl.[7] .................................................. G01M 3/24
(52) U.S. Cl. .......................................... 73/40.5 A; 73/632
(58) Field of Search ............................... 73/40.5 A, 584, 73/592, 632, 658, 660, 1.82, 646; 702/51, 54

(56) References Cited

U.S. PATENT DOCUMENTS

| | | | |
|---|---|---|---|
| 3,222,635 | 12/1965 | Simpkins et al. | 340/15 |
| 3,253,457 | 5/1966 | Pakala et al. | 73/40.5 A |
| 3,592,967 | 7/1971 | Harris | 176/1 A |
| 3,782,180 | 1/1974 | Harris | 73/69 |
| 3,978,915 | 9/1976 | Harris | 165/11 |
| 4,201,087 | 5/1980 | Anita et al. | 73/339 A |
| 4,287,581 * | 9/1981 | Neale, Sr. | 73/40.5 A |
| 4,416,145 | 11/1983 | Goodman et al. | 73/40.5 |
| 4,476,706 | 10/1984 | Hadden et al. | 73/1 G |
| 4,635,042 | 1/1987 | Andrews | 73/40.5 A |
| 4,722,224 | 2/1988 | Scheller et al. | 73/599 |
| 4,727,750 | 3/1988 | Yonemura | 73/592 |
| 4,823,600 | 4/1989 | Biegel et al. | 73/592 |
| 4,835,519 | 5/1989 | Suzaki et al. | 73/632 |
| 4,852,390 | 8/1989 | Fisch | 73/40.5 |
| 4,879,546 | 11/1989 | Dunham et al. | 340/632 |
| 4,945,766 | 8/1990 | Dahlmann et al. | 73/598 |
| 4,981,044 | 1/1991 | Adams et al. | 73/623 |
| 5,053,747 | 10/1991 | Slate et al. | 340/507 |
| 5,205,175 * | 4/1993 | Garza et al. | 73/1.82 |
| 5,351,544 | 10/1994 | Endo et al. | 73/588 |
| 5,445,026 | 8/1995 | Eagen | 73/40.5 A |
| 5,453,932 | 9/1995 | Brabec | 364/424.07 |
| 5,535,136 | 7/1996 | Standifer | 73/40.5 A |
| 5,639,958 | 6/1997 | Lange | 73/592 |
| 5,710,377 | 1/1998 | Youngquist et al. | 73/40.5 A |

* cited by examiner

*Primary Examiner*—John E. Chapman
(74) *Attorney, Agent, or Firm*—Luedeka, Neely & Graham, P.C.

(57) ABSTRACT

A portable digital ultrasonic monitoring system and method for use by an operator in detecting the ultrasonic waves and temperature variations produced by sources such as leaks in pipes, arcing, electrical corona and machinery defects is provided. The digital ultrasonic monitoring system includes a microprocessor based system in a hand held elongate housing that digitally analyzes and stores information received from its sensors. The digital ultrasonic monitoring system provides a referenced decibel output reading of the signal strength of the received ultrasonic signals. In addition, a heterodyned type audio signal that is related to the sensed ultrasonic signals is provided to the operator through a pair of headphones. The portable device has user input keys that allow the operator to select from a variety of different operating modes. A display displays a variety of different readings depending upon the operating mode of the device.

18 Claims, 8 Drawing Sheets

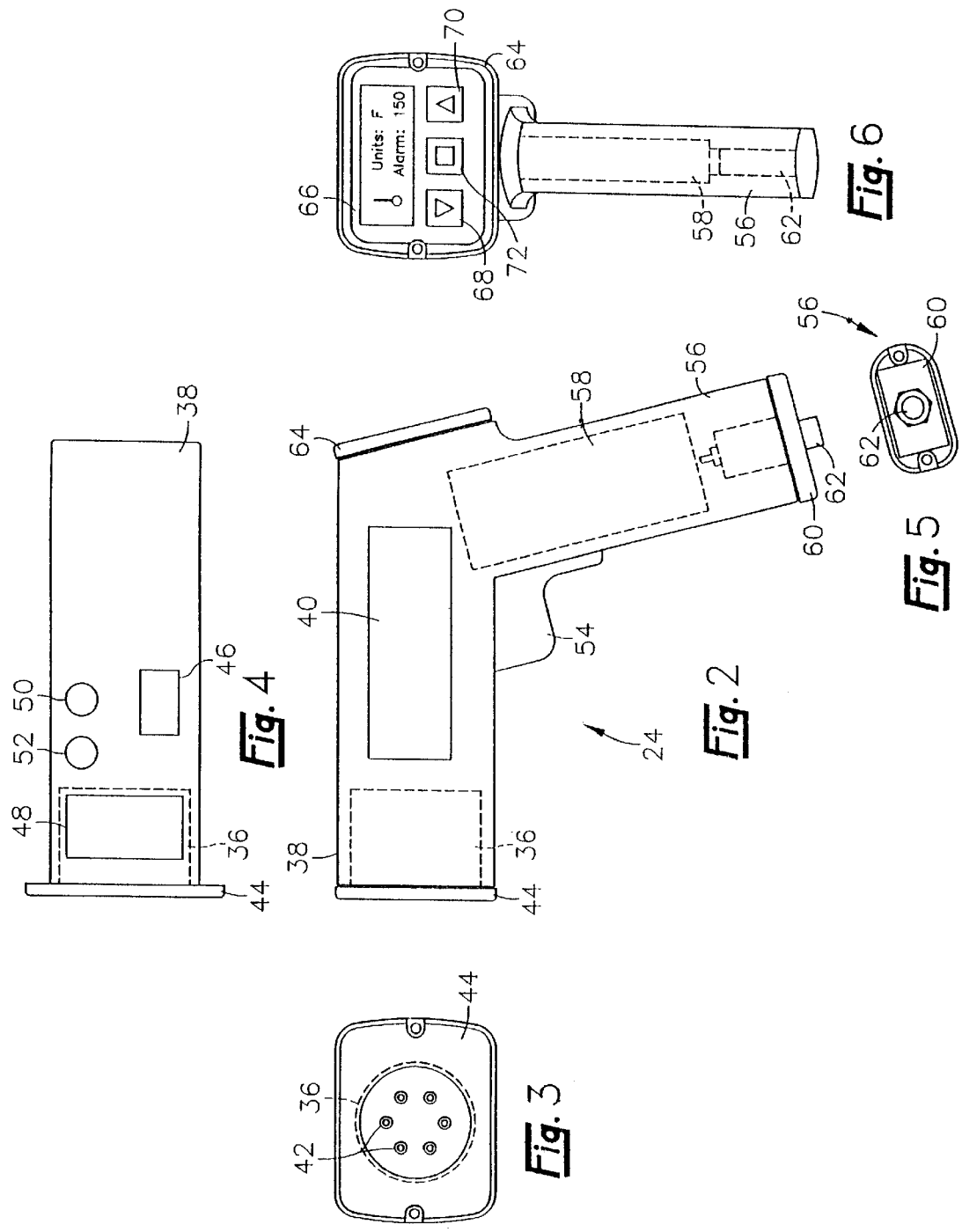

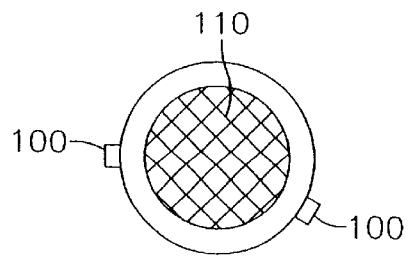
Fig. 9B
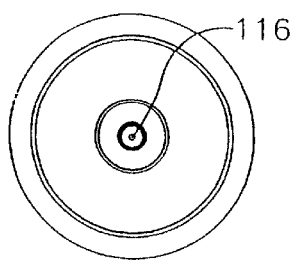
Fig. 10B
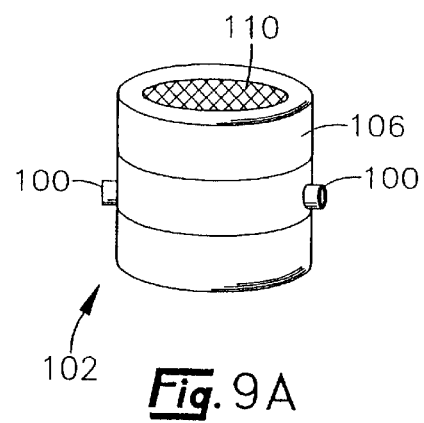
Fig. 9A
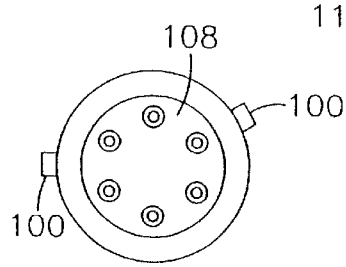
Fig. 10C
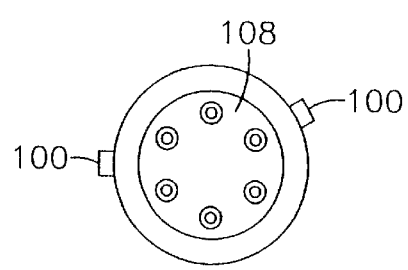
Fig. 9C
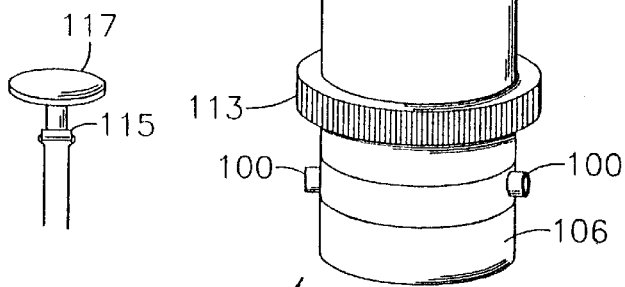
Fig. 10D   Fig. 10A
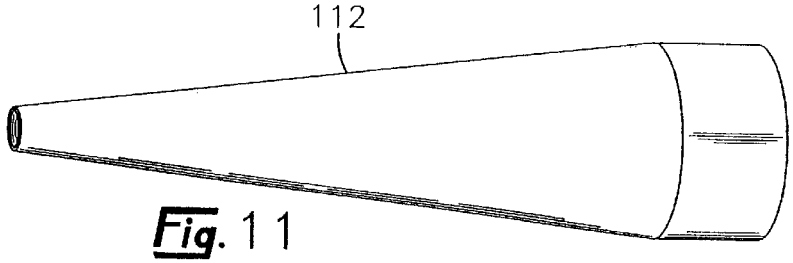
Fig. 11

*Fig.* 12

DIGITAL ULTRASONIC MONITORING SYSTEM AND METHOD

This application is a continuation of application Ser. No. 09/075,560 filed May 4, 1998, abandoned.

BACKGROUND

1. Field of the Invention

In general, the present invention relates to a digital device for detecting and monitoring ultrasonic waves. In particular, the present invention relates to a portable ultrasonic monitoring instrument that utilizes a microprocessor to analyze and store information about detected ultrasonic waves in order to locate leaks and machinery defects.

2. Background of the Invention

The normal frequency range for human hearing is roughly 20 to 20,000 hertz. Ultrasonic sound waves are sound waves that are above the range of human hearing and, thus, have a frequency above about 20,000 hertz. Any frequency above 20,000 hertz may be considered ultrasonic. Most industrial processes, including almost all sources of friction, create some ultrasonic noise. For example, leaks in pipes, machinery defects and electrical arcing produce ultrasonic sound waves that have a frequency that is too high for the human ear to detect. In the past, analog ultrasonic sensors have been used in industrial settings to sense these ultrasonic sound waves. To monitor the ultrasonic sound waves produced by operating machinery, an operator would use an ultrasonic sensor to obtain a reading indicating the strength of the ultrasonic sound waves near the machine. If the ultrasonic sound levels generated by one machine were larger than those produced by another similar machine, the operator would investigate further to determine if a problem existed with the noisy machine. If the ultrasonic sound levels were approximately equal to those produced by a properly functioning machine, the operator would assume the machine was properly functioning and simply proceed to the next machine. Some of the prior art ultrasonic sensors used to monitor machines were semi-permanently mounted on individual machines so that ultrasonic readings could be obtained by simply checking the output of the ultrasonic sensors. However, other ultrasonic detectors were portable to allow the operator to monitor many machines. These portable ultrasonic detectors were especially useful in locating small leaks in pipes carrying pressurized gasses. Because ultrasonic sound waves attenuate very rapidly, the location of the sound waves is usually the location of the leak. Therefore, in order to locate a leak, the user simply moved the ultrasonic detector over the surface until the strength of the ultrasonic sound waves rapidly increased. The user then investigated further by placing soapy water on the location where it was suspected that there was a leak. If a leak was present, bubbles would form in the soapy water where the gas was escaping.

These analog ultrasonic instruments suffer from many drawbacks. For example, the analog instruments do not provide a quantitatively referenced power level of the signal to the user. Instead, the analog ultrasonic units simply provide a relative indication of the ultrasonic sound waves' strength in one location compared to another location. Typically, this information is provided to the user by a needle on a dial with an adjustable volume. The volume is set so that the needle is at a reference point when an ultrasonic measurement is taken in a particular location. If the needle rises above that point when a reading is taken in another location, the ultrasonic noise level is higher at the second location than the reference point and vice versa. This is undesirable because it makes it difficult to compare readings taken at one point in time to readings taken at a later point in time. Also, prior art analog instruments did not employ analog to digital converters or microprocessors, making it difficult for them to perform advanced signal analysis techniques on the ultrasonic electrical signals.

SUMMARY OF THE INVENTION

The present invention eliminates the oversights, difficulties, and disadvantages of the prior art by providing an automated digital ultrasonic monitoring system for use by an operator in detecting ultrasonic signals. The digital monitoring system allows reliable referenced signal strength measurements to be obtained and recorded. In addition, advanced signal processing techniques can be used to analyze the digital data produced.

In accordance with the present invention, a digital ultrasonic sound and temperature detection and analysis device for measuring surface temperatures of an object and detecting ultrasonic sounds produced by sources such as leaks in pipes, arcing, electrical corona and machinery defects is provided. An elongate housing encloses the digital ultrasonic device. The elongate housing has a grip that is designed to provide a handle that allows a user to carry and point the digital ultrasonic device like a pistol. A barrel shaped portion is attached to the grip at one end and has a sensor socket located in the other end. A trigger located at the junction of the barrel and the grip is used to control the functioning of the digital ultrasonic device.

A set of sensors including a temperature sensor; an ultrasonic sensor, and a combination temperature and ultrasonic sensor are provided for use with the ultrasonic monitoring device. A sensor socket located in the barrel shaped portion of the ultrasonic device is designed to interchangeably receive a sensor from the set of sensors. The sensor socket that receives the sensor from the set of sensors has a cylindrical shaped cavity having walls and a bottom portion. A set of pins located in the bottom portion of the sensor socket provides electrical contacts between a plurality of electrical contacts on the sensor installed in the sensor socket and the ultrasonic device. A pair of spaced apart L-shaped grooves are located in the walls of the cylindrical shaped cavity. Each of the L-shaped grooves has an open receiving portion that begins at the rim of the cylindrical shaped cavity and extends a distance down the cavity walls to an ending position and a leg portion that extends perpendicularly from the ending position of the open receiving portion. A pair of protrusions are fixedly attached to the sides of each of the sensors in the set of sensors. The protrusions are shaped and positioned to be received in the L-shaped grooves in a manner that removably secures the sensor in the sensor socket. Installation guide means prevent a sensor from the set of sensors from being improperly installed in the sensor socket. An identification circuit, that contains identification and configuration information concerning the sensor, is located on each sensor in the set of sensors.

A received signal strength indicator receives ultrasonic electrical signals from a sensor installed in the sensor socket that correspond to the ultrasonic sounds detected by the sensor and produces a signal indicative of the strength of the ultrasonic electrical signals. A first voltage controlled amplifier also receives the ultrasonic electrical signals from the installed sensor and amplifies the ultrasonic electrical signals to produce amplified ultrasonic electrical signals. A mixer receives the amplified ultrasonic electrical signals from the first voltage controlled amplifier and local oscillator frequency signals from a variable frequency sine wave oscillator and heterodynes the amplified ultrasonic electrical signals to produce audible frequency range signals that correspond to the amplified ultrasonic electrical signals but are in the audible frequency range of a human being. A low pass filter receives the audible frequency range signals from the mixer and removes any above audible range frequency signals in the audible frequency range signals received from the mixer. Next, a second voltage controlled amplifier receives and amplifies the audible frequency range signals after the audible frequency range signals have passed through the low pass filter. From there, the amplified audible frequency range signals are sent to a headphone jack located on the base of the grip. A pair of headphones have a headphone plug that receives the amplified audible frequency range signals from the headphone jack when the headphone plug is inserted into the headphone jack and broadcasts the audible frequency range signals so that they can be heard by a user of the digital ultrasonic device. A temperature reading is provided by a temperature sense circuit that sends a constant current to the installed temperature sensor and creates a temperature signal that corresponds to the temperature sensed by the sensor.

In an especially preferred embodiment, user control of the digital ultrasonic monitoring device is provided by a series of inputs and a display. A mode key user input located on the elongate housing allows the user to select an operating mode for the digital ultrasonic device. An up arrow key and a down arrow key user input allow the user to enter commands that control functions such as the frequency range in which the digital ultrasonic device will operate and the gain of the first and second voltage controlled amplifiers. A display, preferably an LCD, displays a received signal strength bar graph, a received signal strength level, a temperature reading, a battery level indicator, and a monitoring frequency value in an easily readable format.

Analysis of the sensed data and control of the digital ultrasonic monitoring device's functions are further provided by a microprocessor that receives and analyzes the signals produced by the sensors. Examples of the inputs received by the microprocessor include the signal indicative of the strength of the ultrasonic electrical signals from the received signal strength indicator, the audible range frequency signal from the mixer, the identification and configuration information from the sensor installed in the sensor socket, and the temperature signal from the temperature sense circuit. The microprocessor also loads firmware upgrades, monitors the power remaining in the battery, controls the first and second voltage controlled amplifiers, configures the ultrasonic monitoring device to operate with the sensor installed in the sensor socket, controls the frequency of the variable frequency sine wave oscillator, provides control signals to the display, and performs analog to digital conversions. The information received by the microprocessor is then used to calculate an instantaneous signal level that represents the peak ultrasonic sound level received in a given time period, a peak hold signal level that represents the peak ultrasonic sound level received between the time the trigger was pressed and the time the trigger was released, an averaged signal level that represents the running average of the ultrasonic sound level, and a peak factor signal level that represents the difference between the peak hold level and the averaged signal level. Based on these calculated values, the microprocessor selectably produces an alarm signal when the instantaneous signal level, peak hold signal level, peak factor signal level, averaged signal level, or temperature signal exceeds a user-defined alarm level. These alarm signals are sent to the headphones. Preferably, the microprocessor also produces a signal clipping alarm signal that indicates the gain of the first voltage controlled amplifier should be decreased because the received ultrasonic electrical signals are so strong that the ultrasonic electrical signals are being clipped by internal electronics such as the mixer. A memory is used to selectably store information concerning the sensed ultrasonic signals and configuration parameters for the set of sensors.

A communications port located underneath the barrel shaped portion of the elongate housing allows the microprocessor and memory in the digital ultrasonic device to communicate with a host computer. A signal output provides a signal that is the detected envelope waveform of the ultrasonic signal. This signal consists of instantaneous points on the waveform that have a DC value directly related to the signal strength in decibels of the ultrasonic electrical signal at that point. This signal output can be provided to a machine analyzer so that frequency and time domain analysis can be performed on the ultrasonic envelope waveform. Preferably, an infrared communications port is provided that allows the digital ultrasonic device to wirelessly communicate with an external infrared communications port located on another device.

In addition to detecting ultrasonic sounds produced by objects such as machines, the digital ultrasonic device may be used to detect holes in objects that are not radiating ultrasonic noise. This is accomplished by placing an ultrasonic tone generator that produces an ultrasonic tone into a vessel, pipe or container that is being checked for holes or leaks. By locating the ultrasonic sound escaping from the vessel, a user of the device can locate a hole in the vessel.

The preferred ultrasonic monitoring device is powered by a rechargeable power supply located in the grip of the elongate housing. A battery charger jack located underneath the barrel of the elongate housing receives a voltage that is used to recharge the rechargeable power supply.

Another preferred embodiment of the present invention includes a portable device for detecting and analyzing ultrasonic sounds. The device is contained in an elongate housing that is designed to be hand held. The device is operated by depressing a trigger. An ultrasonic sensor senses ultrasonic sounds and produces ultrasonic electrical signals. A digital processing means receives and digitally analyzes the ultrasonic electrical signals. Output means communicate the results of the digital analysis to a user of the device. In an especially preferred embodiment, the output means further comprise a pair of headphones that communicate with the device and broadcast audible signals corresponding to results of the digital analysis. In addition, the digital processing means produces visual or audible alarms to alert a user of the device that certain parameters have been exceeded. The digital processing means can also be reprogrammed in the field to incorporate firmware updates. A referenced decibel value of the ultrasonic electrical signals is provided to the output means by determining an amplitude envelope of the ultrasonic electrical signals and measuring an instantaneous DC voltage value of the amplitude envelope. Preferably, the referenced decibel value is determined by comparing the measured signal amplitude against a stored look up table of calibration values, a zero decibel value being referenced to an acoustic sound pressure level of 20 microPascals or 0.0002 microBars in an especially preferred embodiment. A memory stores and provides digital representations of the ultrasonic electrical signals.

A preferred method of detecting leaks, arcing, electrical corona or machinery defects is also provided in accordance with the present invention. The method involves receiving ultrasonic sound waves from an area in which a leaks, arcing, electrical corona or machinery defect may be present. In an alternate embodiment, ultrasonic sound waves are produced on one side of a barrier or inside of a container and an attempt is made to receive the produced ultrasonic sound waves on the other side of the barrier or outside of the container. A set of digital data representing the received ultrasonic sounds is produced. The data is digitally analyzed to determine if a leak opening or other defect is present in the area from which the ultrasonic sound waves were received. In addition, frequency and time domain analysis are performed on the digital data to determine the presence of machine faults or imperfections. Furthermore, the digital data representing the ultrasonic sound waves is stored so that it can be retrieved when necessary. The amplitudes of peaks occurring in the ultrasonic sounds are also examined to determine the likelihood a leak or machinery defect is present. Preferably, a referenced decibel value of the received ultrasonic sounds is also determined by digitally analyzing the data. The temperature of the area in which a machinery defect or leak may be present is also measured and recorded. The results of the digital analysis of the data are visually displayed and audibly indicated.

Yet another embodiment of the present invention includes an apparatus for detecting machinery defects or leaks in containers and pipes. A sensor socket interchangeably receives a sensor from a set of sensors. Attachment means removably secure the sensors from the set of sensors in the sensor socket. An ultrasonic sensor detects ultrasonic sound waves and produces sensed ultrasonic electrical signals. A temperature sensor measures surface temperatures and produces sensed electrical temperature signals. A microprocessor digitally analyzes the sensed ultrasonic electrical signals and the sensed electrical temperature signals. In addition, time and frequency domain waveform analysis are performed on the ultrasonic electrical signals. Alarm means indicate when the ultrasonic electrical signal exceeds a user selected threshold value. Display means display properties of the ultrasonic electrical signals and the electrical temperature signals. In an especially preferred embodiment, the display means is a liquid crystal display. Mixing means mix the ultrasonic electrical signals received by the ultrasonic sensor with a second signal to produce a third signal that is related to the ultrasonic waves detected by the ultrasonic sensor. To detect holes in containers that are not radiating ultrasonic waves, an ultrasonic sound wave generator is placed inside of an object so that ultrasonic sound waves will escape from any openings in the walls of the object.

Other objects, features and advantages of the present invention will become apparent by reference to the following detailed description when considered in conjunction with the accompanying drawings.

BRIEF DESCRIPTION OF THE DRAWINGS

In the drawings below, like reference characters refer to like parts throughout the several views, and wherein:

FIG. 2 is a side view of the elongate housing that shows the locations of the main internal components;

FIG. 3 is a front view of the elongate housing that shows the bottom of the sensor socket;

FIG. 4 is a bottom view of the barrel shaped portion of the elongate housing that shows the location of the input and output ports.

FIG. 5 is a bottom view of the grip portion of the elongate housing showing the headphone jack;

FIG. 6 is a rear view of the elongate housing that shows the display and user input keys;

FIGS. 9a, 9b, and 9c are pictorial representations of an airborne sensor;

FIGS. 10a, 10b, 10c, and 10d are pictorial representations of a contact sensor;

FIG. 11 is a pictorial representation of a focusing cone;

DESCRIPTION OF THE PREFERRED EMBODIMENT(S)

The ultrasonic monitoring system of the present invention effectively locates leaks of air, steam, or other gases from pressurized systems as well as arching and electrical corona, which may produce ultrasonic sounds. Furthermore, the ultrasonic monitoring system can also diagnose and analyze steam trap operation, bearing and gear defects, cavitation and surging in pumps and compressors, lubrication problems in dynamic equipment, valve operation, steam lines, and piston friction and detonation problems in reciprocating equipment.

Figure 1:
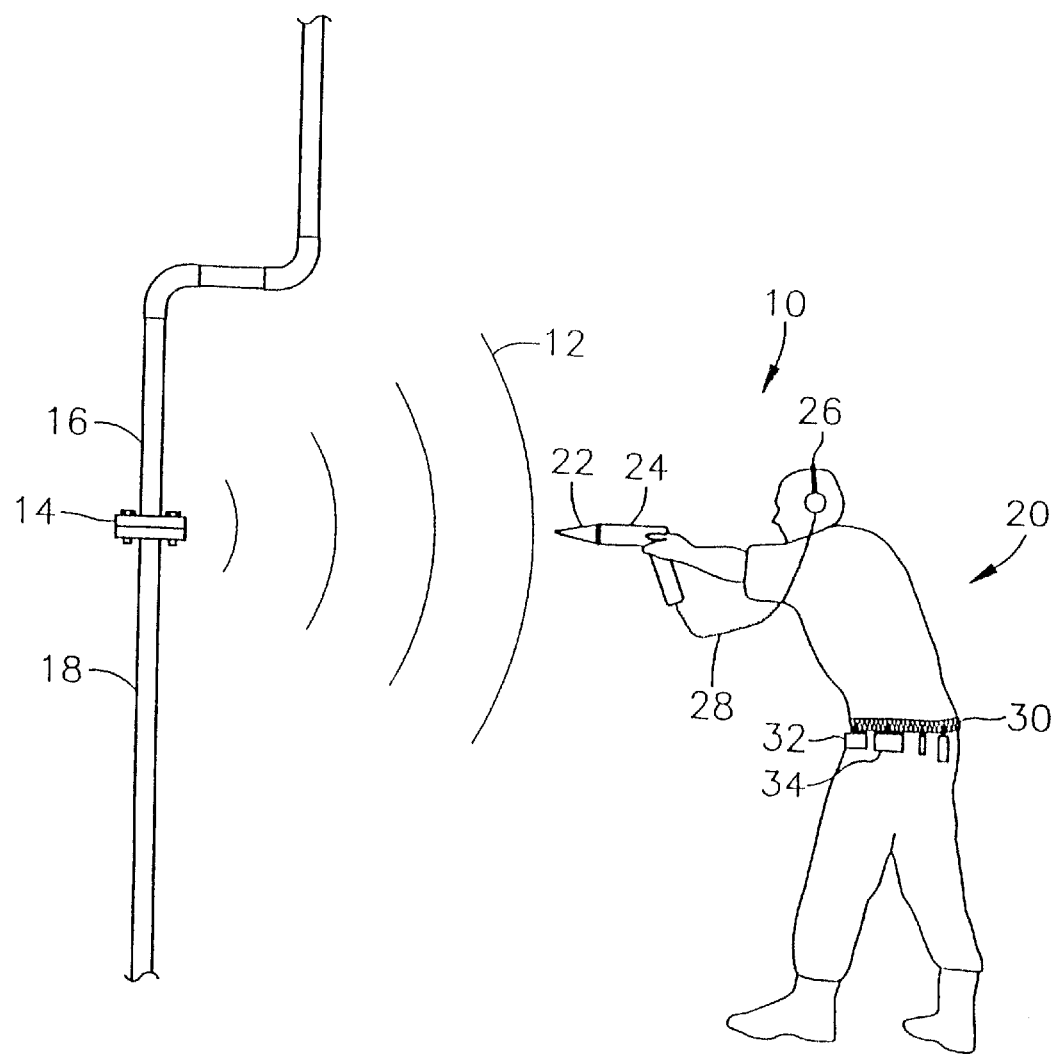
FIG. 1 is a perspective view of an operator using the ultrasonic monitoring system of the present invention.

Referring now to FIG. 1, an especially preferred ultrasonic monitoring system 10 for detecting and monitoring ultrasonic sound waves 12 is shown. The ultrasonic sound waves 12 are emanating from the intersection 14 of two abutting pipes 16 and 18. In the case of leak detection, the ultrasonic monitoring system 10 is principally used by the operator 20 to determine the location from which the ultrasonic sound waves 12 are emanating. The ultrasonic monitoring system 10 consists of an ultrasonic sensor 22 mounted in a portable elongate housing 24. In operation, the elongate housing 24 is held by the operator 20 and pointed toward a machine or device that might contain a leak or defect that is radiating ultrasonic sound waves 12. A pair of headphones 26 are worn by the operator 20 and attached to the elongate housing 24 via a cord 28. The operator 20 of the ultrasonic monitoring system 10 receives an audible signal the volume of which indicates the relative strength of the ultrasonic sound waves 12 being received by the sensor 22 located in the barrel of the elongate housing 24 through the pair of headphones 26. When the elongate housing 24 and the sensor 22 are pointed away from the source 14 of the ultrasonic sound waves 12, the strength of the ultrasonic sound waves 12 detected by the sensor 22 decreases. When the elongate housing 24 and the sensor 22 are pointed toward the source 14 of the ultrasonic sound waves 12, the strength of the ultrasonic sound waves 12 detected by the sensor 22 increases. This increase and decrease in the detected ultrasonic sound wave strength can be audibly represented in a variety of fashions. For example, a rise in the volume of a tone produced by the ultrasonic monitoring system 10 could indicate the detected ultrasonic sound waves are growing stronger and a fall in the volume of the tone could indicate the sound waves are growing weaker. A rise and fall in the pitch of the tone could also indicate a respective rise and fall in the strength of the detected ultrasonic sound waves. Alternatively, a Geiger counter type clicking would also serve the function of indicating the strength of the detected sound waves to the user 20 of the ultrasonic monitoring system 10. However, in a most preferred embodiment, the ultrasonic sound waves 12 received by the sensor 22 are heterodyned to produce related electrical signals that have a frequency in the audible range of humans. These related signals have many of the distinctive properties of the ultrasonic sound waves 12 from which they were produced. Providing these related electrical signals to the headphones 26 allows the operator 20 to identify the type of noise source radiating the ultrasonic sound waves 12 by listening to the distinctive noise signals created by different types of ultrasonic sound wave sources.

The ultrasonic sound waves 12 received by the sensor 22, or the data derived from the ultrasonic electrical signals produced by the sensor 22, are preferably stored in a microprocessor based system 32, which is releasably secured to the operator 20. The microprocessor based system 32 is used to store and analyze the data collected by the ultrasonic monitoring system 10, provide testing information to the operator 20 and prompt the operator 20 to take measurements from particular locations. As discussed in greater detail below, the microprocessor based system 32 in a preferred embodiment is a portable personal computer or personal data assistant. The microprocessor based system 32 is secured to the operator 20 via a utility belt 30. The utility belt 30 also has a holster for receiving the elongate housing 24, pockets for accessories such as small tools, tags, survey tape and soap solutions, and an ultrasonic sound wave transmitter and charger 34.

The elongate housing 24 contains many of the components needed to implement an ultrasonic monitoring device 10 in accordance with the present invention. The preferred internal location of these components inside the elongate housing 24 is shown in FIG. 2. A sensor socket 36 is located in the barrel portion 38 of the elongate housing 24. The sensor socket 36 is designed to receive a variety of different sensors 22. When a sensor 22 is installed in the sensor socket 36, the sensor socket 36 provides electrical contact between the installed sensor 22 and a microprocessor based control circuit 40 also located in the barrel portion 38 of the elongate housing 24.

As shown in FIG. 3, the electrical contacts between the sensor 22 and the sensor socket 36 are provided by a series of electrical contacts 42 located in the sensor socket 36. In an especially preferred embodiment, the electrical contacts 42 consist of six spring biased pins 42 that create an electrical connection between the pins 42 and corresponding contact pads 108 located on the base of the sensors 22. The sensor socket 36 is surrounded by a plate 44 that covers and protects the front of the barrel portion 38 of the elongate housing 24.

The microprocessor based control circuit 40 is internally contained in the barrel portion 38 of the elongate housing 24. Preferably, the microprocessor 78 in the microprocessor based control circuit 40 is a sixteen bit Toshiba microprocessor having model number TMP93CS41F. The microprocessor based control circuit 40 also preferably contains a RAM chip that is 256 K X 8 bits and a flash memory that is 64 K by 8 bits. The microprocessor based control circuit 40 can communicate to external devices by means of several input and output ports located on the lower portion of the barrel 38 of the elongate housing 24. As shown in FIG. 4, an RS 232 port 46 is located on the lower portion of the barrel 38. In addition to the RS 232 port 46, an infrared communications port 48 is also located on the lower portion of the barrel 38 beneath the sensor socket 36 and provides the microprocessor control circuit 40 the ability to establish wireless communication with an external device. Preferably, the infrared communications port 48 is a low-voltage infrared receiver manufactured by Texas Instruments under Model No. TIR1000. Additionally, a signal output port 50 is located near the RS 232 port 46 and the infrared communications port 48. The signal output port 50 provides a signal that is the detected envelope waveform of the ultrasonic electrical signal. The detected envelope waveform signal consists of any instantaneous point on the detected waveform having a DC value directly related to the signal strength in decibels at that point. This signal output may be provided to a machine analyzer so that frequency and time domain analysis can be performed on the ultrasonic envelope waveform. The final port shown in FIG. 4 is a battery charger jack 52 that is used to receive the DC voltage source that charges the rechargeable power supply 58.

Referring back to FIG. 2, a trigger 54 for activating the ultrasonic monitoring system 10 is located at the junction of the barrel portion 38 and the grip portion 56 of the elongate housing 24. The trigger 54 is positioned similar to a trigger on a real pistol and is electrically connected to the microprocessor control circuit 40. When the trigger 54 is pressed, the ultrasonic monitoring system 10 begins collecting data When the trigger 54 is released, the system 10 ceases collecting data. Thus, the trigger 54 simply functions as an activation switch and it is understood that there are alternative manners in which this function could be implemented The electrical components of the ultrasonic monitoring system 10 contained in the elongate housing 24 are powered by a rechargeable power supply 58 that is mounted in the grip portion 56 of the elongate housing 24. As previously discussed, the rechargeable power supply 58 is recharged by a way of a battery charger jack 52 which is located next to the signal output port 50. A standard adapter having a first end for plugging into a common electrical outlet and a second end for engaging port 52 provides power to the battery charger jack 52. A headphone jack 62 located on the bottom portion of the grip 56 extends through the handle plate 60 of the elongate housing 24. The headphone jack 62 provides signals to the headphones 26 through a removable cord 28 that is electrically connected to the headphones 26. Alternatively, wireless headphones may be incorporated into the present invention. FIG. 5 is a view of the bottom of the grip 56 that clearly shows the headphone jack 62 and the handle plate 60.

FIG. 6 shows the rear plate 64 of the elongate housing 24 that contains the display 66 that is viewed by the operator 20 when ultrasonic data measurements are being taken. The display 66 is mounted in the rear plate 64 and provides visual ultrasonic data indicators and operational information to the operator 20 of the ultrasonic monitoring system 10. The display 66 is preferably a 2×12 character matrix liquid crystal display. A down arrow user input key 68, an up arrow user input key 70 and a mode user input key 72 are located below the display 66. The grip 56, the headphone jack 62 and the internal rechargeable power supply 58 are also shown in FIG. 6.

Figure 7A:
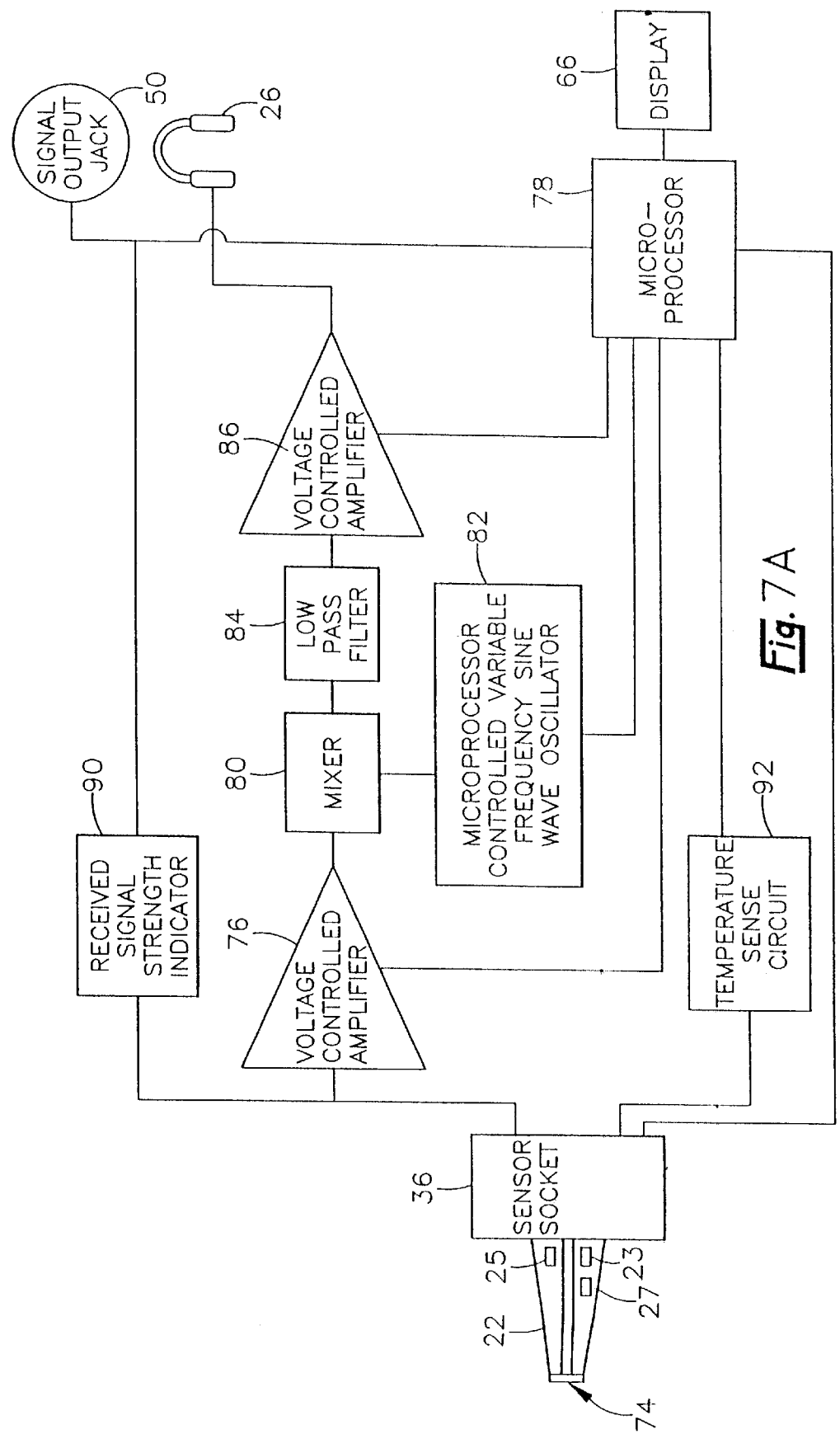
FIG. 7a is a block diagram of the electronics contained in the elongate housing.

The functioning of the electrical components inside the elongate housing 24 can better be understood by examining a block diagram of the components. The embodiment shown in FIG. 7a has a ultrasonic sensor 22 with an integral temperature sensor 74 installed in the sensor socket 36. In a preferred embodiment, the temperature sensor 74 is coaxially mounted inside the cavity of the ultrasonic sensor 22. The ultrasonic sensor 22 with the integral temperature sensor 74 provides ultrasonic electrical signals to the electrical contacts 42 in the sensor socket 36. The sensor socket 36 provides the ultrasonic electrical signal that is related to the strength of the ultrasonic sound waves 12 received by the ultrasonic sensor 22 to a first voltage controlled amplifier 76. The amount of amplification provided by the first voltage controlled amplifier 76 is controlled by a microprocessor 78. After being amplified, the amplified ultrasonic electrical signal is sent to a mixer 80. The mixer 80 mixes the amplified ultrasonic electrical signal with an oscillation signal provided by a microprocessor controlled variable frequency sine wave oscillator 82 to produce a signal that is related to the original ultrasonic electrical signal produced by the ultrasonic sensor 22. This signal consists of at least: (1) the amplified ultrasonic electrical signal; (2) the oscillator signal; (3) the frequency sum of the ultrasonic electrical signal and the oscillator signal; and (4) the frequency difference of the ultrasonic electrical signal and the oscillator signal. The signal output from the mixer 80 is passed through a low pass filter 84 to remove any high frequency components above the audible frequency range of a human being. This filtered signal is then sent to a second voltage controlled amplifier 86 that is controlled by the microprocessor 78. Finally, the amplified and filtered signal is sent to the headphones 26 where it is broadcast to the operator 20. The point is to create a signal that can be heard by humans and is related to the ultrasonic electrical signals in a manner that allows the operator 20 to distinguish between different ultrasonic electrical signals by distinguishing between the different mixed signals. The second voltage controlled amplifier 86 is essentially a volume control for the head phones 26.

An advantage of the ultrasonic monitoring system 10 of the present invention is that there are two signal paths for the ultrasonic electric signals produced by the ultrasonic sensor 22. As discussed above, one signal path provides an audio output that can be listened to by the operator 20 of the ultrasonic monitoring system 10. However, the ultrasonic electrical signal received from the ultrasonic sensor 22 is also sent to a received signal strength indicator 90. The received signal strength indicator 90 is a functional part of a Philips Semiconductor RF Communications Products Model SA637 low-voltage IF receiver. This received signal strength indicator produces an envelope waveform of the ultrasonic electrical signal consisting of instantaneous points on the waveform having a DC value related to the signal strength in decibels of the ultrasonic electrical signal at that point.

Figure 7B:
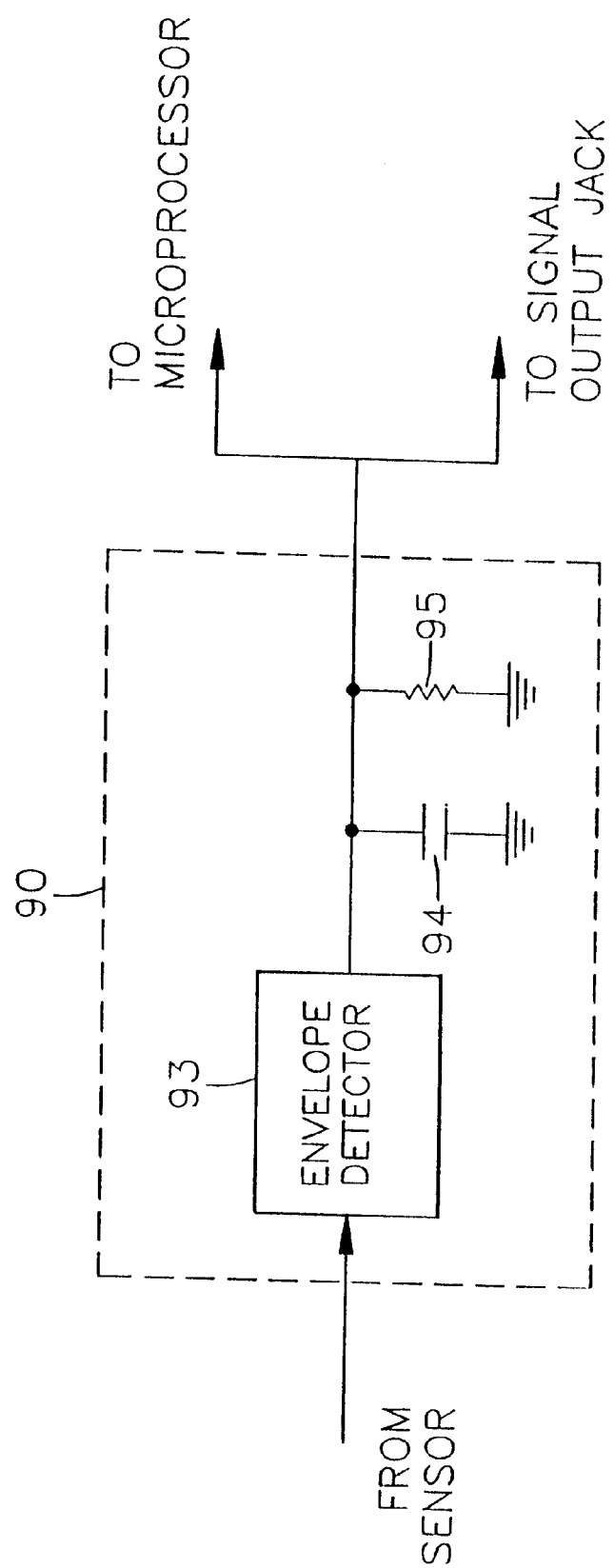
FIG. 7b is a block diagram of an embodiment of a received signal strength indicator.

Referring now to FIG. 7b, an embodiment of the received signal strength indicator 90 is depicted. The signal from the sensor is received by an envelope detector 93. A capacitor 94 and a resistor 95 provide the envelope detector 93 with a rapid rise and slow decay output. In an especially preferred embodiment, the envelope detector 93 is provided with a response time constant of approximately 60 microseconds. The time constant is selected to substantially eliminate the intrinsic ultrasonic frequency signals while allowing any dynamic amplitude variations in those signals to be sent to microprocessor 78. The same signal is also provided to output jack 50. Sampling of this envelope waveform allows the microprocessor 78 to calculate a referenced decibel level of the ultrasonic sound waves at substantially any point in time. The referenced decibel level is determined by comparing the measured signal amplitude against a stored look up table of calibration values, a zero decibel value being referenced to an acoustic sound pressure level of 20 micro-Pascals (0.0002 microbars) in an especially preferred embodiment.

Determining a referenced decibel output is a substantial improvement over the prior art method of using an analog instrument to provide a relative indication of the amplitude of the ultrasonic sound produced in one location compared to the ultrasonic sound produced at another location. Because there is no absolute reference for the prior art ultrasonic measurements, it is difficult to compare a current reading to a prior reading taken at some earlier time. Furthermore, the unreferenced readings taken by one particular instrument are difficult to compare to the readings taken by another instrument. However, because the referenced decibel outputs of an instrument constructed in accordance with the present invention are referenced to a known value, the referenced outputs of the present invention may be stored and accurately compared to later readings obtained by other instruments. Thus, providing a referenced output allows measurements taken over an extended period of time to be analyzed to determine if the amount of ultrasonic sound produced by a particular machine is increasing or decreasing.

The aforementioned envelope detection process could be referred to as a peak follower technique or, when used in conjunction with a filtering time constant, as a form of demodulation. In addition, the envelope detection process may be combined with an analog sample and hold circuit, or, in an especially preferred embodiment, with an analog to digital converter. The technique provides an energy waveform of periodic bursts or rings that represents the bursts or rings of acoustic vibrations. Depending upon the type of machinery faults generating them, these bursts may have a duration of a few milliseconds or less. The intrinsic frequency of the bursts is relatively high, usually several kHz or higher. In the case of the present invention, 40 kHz is the preferred frequency of operation. The idea is to measure the peak amplitude of the burst or ring frequencies during sample time windows. In general, the intrinsic frequency or frequencies of the bursts are not of interest. It is the signal amplitudes and signal periodicity that are of the greatest interest for analysis. Nevertheless, the technique is still of value with ultrasonic sound waves of constant amplitude and constant duration, as may be the case with a steady leak from a pipe. In the case of a constant amplitude ultrasonic sound wave, the envelope waveform would be a DC value representative of the decibel level of the ultrasonic sound wave.

While we use envelope detection as shown in FIG. 7B, it is expressly understood that the Peak Vue techniques disclosed in U.S. application Ser. No. 08/840,844 filed Apr. 17, 1997 which is a continuation of U.S. application Ser. No. 08/555,296 filed Nov. 8, 1995 and now abandoned may be used in accordance with an embodiment of the present invention. Both techniques perform a peak follower function and are able to capture peak amplitude values of short duration signal bursts or rings. Thus, it would be possible to incorporate the Peak Vue method into the present invention.

The output from the integral temperature sensor 74 is provided to the temperature sense circuit 92. The temperature sense circuit 92 supplies a constant current to the temperature sensor 74. The resistance of the temperature sensor 74 is dependent upon its temperature. Thus, the voltage produced by the constant current flowing through the temperature sensor 74 is representative of the temperature sensed by the temperature sensor 74. This voltage is provided to the microprocessor 78 which interprets the voltage as a temperature and sends a temperature reading to the display 66.

The microprocessor 78 uses the signal indicative of the strength of the received ultrasonic sound waves to calculate a number of values. The value calculated by the microprocessor 78 depends upon the mode in which the ultrasonic monitoring system 10 is operating. The operator 20 can select from different operating modes by selecting the operating mode menu with the mode key user input 72 and then scrolling through the mode menu with the up 70 and down 68 arrow input keys. Once an operating mode has been selected by the operator 20, a symbol appears on the display 66 indicating the mode in which the ultrasonic monitoring system 10 is operating.

For example, if the user 20 selects the peak hold mode, the highest input signal level received by the microprocessor 78 from the received signal strength indicator 90 is retained and displayed as long as the trigger 54 remains depressed. When the trigger 54 is released, the peak value of the signal received by the microprocessor 40 is frozen on the display 66. The display 66 and the retained peak value are reset to zero when the trigger 54 is pressed again. Another mode which can be selected is the instantaneous averaging mode. This is the preferred operating mode of the present invention. In this mode, the microprocessor 78 receives the signal indicative of the received ultrasonic electrical signals strength and determines the strength of the ultrasonic sound waves. In a similar fashion to that of the peak hold operating mode, the microprocessor 78 retains and displays the strongest signal received. However, in the instantaneous mode of operation, this value is rapidly reset. Preferably, the display 66 is updated at least three times a second. This allows an almost instantaneous indication of the strength of the ultrasonic sound waves being received by the ultrasonic sensor 22. Yet another mode of operation is the averaged mode. In this mode, the microprocessor 78 calculates and sends to the display 66 an average referenced decibel level of the ultrasonic sound waves received between the time the trigger 54 was pressed and the current time. When the trigger 54 is released, the output is frozen. The decibel level is referenced to an accepted standard, such as zero decibels at an acoustical sound pressure level of 20 microPascals or zero decibels at $50 \times 10^{-12}$ inches peak to peak of mechanical displacement. Still another mode of operation is the peak factor mode of operation. In accordance with this mode, the difference between the peak value of the signal and the average value of the signal is displayed. It is readily appreciated that a number of other values representing various characteristics of the sensed ultrasonic sound waves could be calculated by the microprocessor 78. In fact, one of the primary advantages of using a microprocessor based system is that the manner in which the digital data is analyzed and manipulated can easily be altered without requiring complex design changes. The particular values discussed are simply those of an especially preferred embodiment of the present invention.

The microprocessor 78 also allows an operator of the ultrasonic monitoring system 10 to enter various information concerning the results of the ultrasonic tests for later reference. For example, after the operator has performed a test, the microprocessor 78 can prompt the operator to input information concerning characteristics of the sound produced in the headphones 26 by displaying a message such as "Sounds Like?" on the display 66. The user would then use the up arrow input key 70 and the down arrow input key 68 to scroll through a list of choices such as "buzz", "hiss", "crackle", "pop", "impacting", etc. Once the user has located the proper description, the microprocessor 78 can be instructed to save the description in memory by pressing the mode input key 72. It should be readily understood that a variety of other information could be stored using the above described method.

The ultrasonic sensor 22 and the temperature sensor 74 contain identification information that is read by the microprocessor 78 located in the elongate housing 24. The identification information is sent by an identification circuit 23 in the sensors 22 and 74 to the microprocessor 78. The microprocessor 78 uses the identification information to configure the ultrasonic monitoring system 10 to operate using the type of sensor 22 installed in the sensor socket 36. The identification circuit 23 preferably consist of a memory with a serial output. Preferably, the identification information not only identifies the type and nature of the sensors 22 and 74, but also includes calibration data used by the device 10 to accurately interpret the sensors 22 and 74 signals.

In an especially preferred embodiment, the identification circuit 23 is a DS2502 1 KBIT Add-Only Memory manufactured by Dallas Semiconductor. Alternatively, the identification circuit 23 is a resistor having a resistance value that corresponds to a particular sensor 22 and 74. The microprocessor 78 determines the type of sensor 22 and 74 by determining the value of the resistor. In yet another embodiment, the identification circuit 23 is a bar graph containing visually encoded information that is read by an optical sensor located in the sensor socket 36.

Figure 8A:
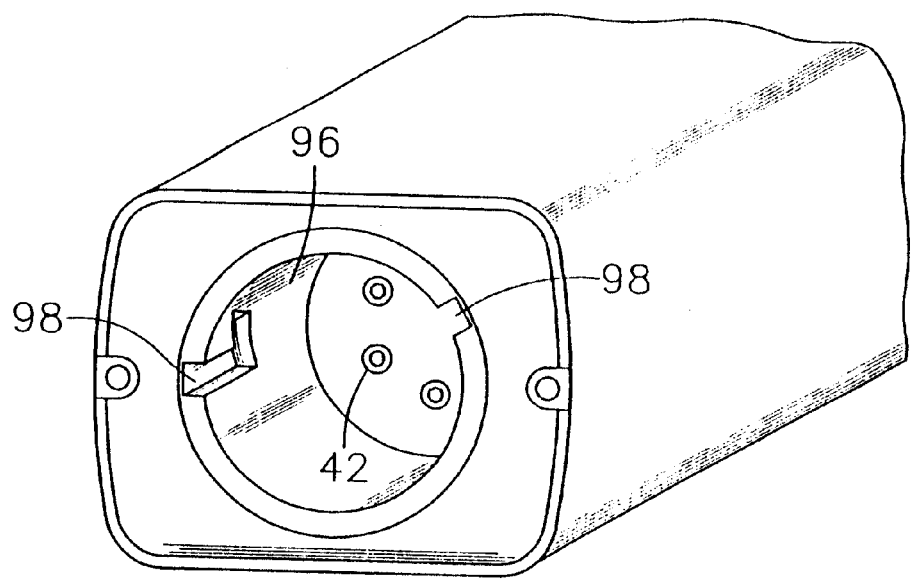
FIGS. 8a and 8b are pictorial representations of a preferred sensor socket.
Figure 8B:
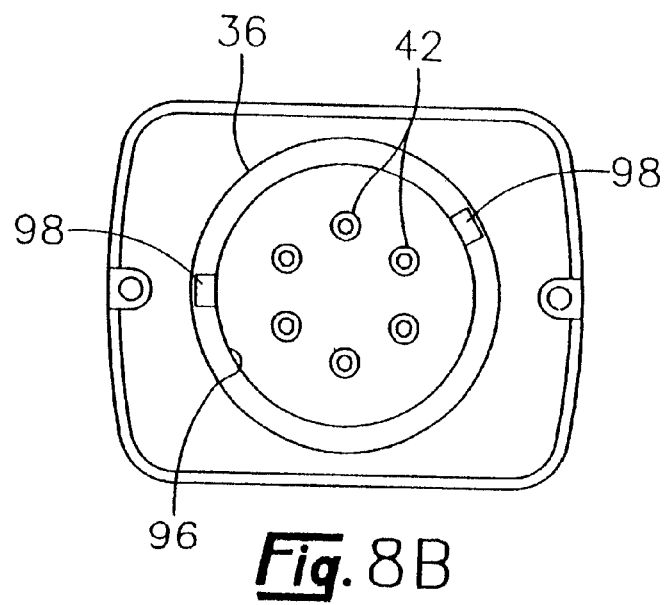

The sensor socket 36 is preferably designed to allow the ultrasonic monitoring system 10 to interchangeably use different types of sensors 22. As shown in FIGS. 8a and 8b, the sensor socket 36 preferably consists of a cylindrical chamber 96 for receiving the sensors 22 with a set of electrical contact pins 42 in the bottom of the cylindrical chamber 96 that are in electrical contact with corresponding contact pads 108 on a sensor 22 that has been installed in the sensor socket 36. In an especially preferred embodiment, six pins 42 in the sensor socket 36 electrically connect the sensor 22 to the ultrasonic monitoring device 10. Two of the pins 42 are used to send the received ultrasonic electric signals to the voltage controlled amplifier 76 of the heterodyning audio circuit and the received signal strength indicator 90. Two pins 42 are used to provide a power supply voltage and a power supply ground to the installed sensor 22. One of the pins 42 is used to provide a temperature reading to the temperature sense circuit 92 and, the last pin 42 is used to provide a communication line between the identification circuit 23 on the sensor and the microprocessor control circuit 78 in the elongate housing 24. It is understood that more electrical connections could be provided if necessary. Each of the pins 42 are spring biased and move axially to yieldably engage the contact pads 108.

The sensors 22 are held in the sensor socket 36 by a pair of protruding members 100 that are designed to be received by corresponding channels 98 in the walls of the cylindrical sensor socket 36. In an especially preferred embodiment, the channels 98 are L-shaped so that the sensor 22 is installed in the sensor socket 36 by inserting the protruding members 100 into the top of the L-shaped channels 98 and pushing the protruding members 100 down into the channels 98. The sensor is then twisted so that the protruding members 100 are securely contained in the leg of the L-shaped channels 98 and prevent the sensor 22 from being removed from the sensor socket 36. The process is remotely similar to placing a bayonet on the end of a rifle.

The sensor 22 can only be inserted into the sensor socket 36 with the protrusions 100 on the sensor 22 aligned with the grooves 98 in the socket 36. Because it is important that the contact pins 42 in the sensor socket 36 be aligned with the proper contact pads 108 of the sensor 22, the protruding members 100 are preferably positioned so that it is mechanically impossible to install the sensors 22 oriented in the wrong fashion. For example, if the protruding members 100 are placed directly across from each other, there are two possible ways to insert the sensor 22 into the socket 36. Therefore, the protruding members 100 are preferably positioned so that they are not directly across from one another. This insures that the contact pins 42 in the socket 36 are properly aligned with the contact pads 108 of the sensor 22. It is understood that a number of other mechanical means could be used to key the sensors 22 to help insure proper insertion, however, the aforementioned approach is easy to implement and quite effective.

A wide variety of ultrasonic sensors 22 can be installed in the sensor socket 36 depending upon the particular needs of the operator 20. While it is appreciated that there are numerous applications for an ultrasonic monitoring system 10, machinery monitoring and leak detection are the primary uses for the ultrasonic monitoring system 10 of the present invention. The frequency range of interest for these applications is approximately 20 to 100 kHz. Conventionally, 40 KHz has been used by several manufacturers of ultrasonic instruments as the primary frequency of interest. This is probably the best general purpose frequency range, as it is high enough to be above most loud low frequency machine vibrations yet not so high as to be severely attenuated at reasonable distances. It should be understood that the ultrasonic sound waves produced by machinery defects or leaks typically do not consist of a single tone or pitch. These sounds are broadband signals that consist of many different frequencies. It is the complex nature of the signals that allows a trained operator to distinguish between the heterodyned ultrasonic sounds produced by different conditions. For example, leaks in pressurized containers generally create a rushing sound while arcing and electrical corona typically produce a cracking or buzzing sound. In addition to differences in the sounds that can be audibly detected by listening to the heterodyned signal, a machine analyzer can analyze the frequency spectrums of the waveforms to detect signal spiking caused by bearing defects or other impact producing conditions. Because of the wide range of applications, it is understood that a variety of different sensors 22 designed to detect a range of different frequencies could be utilized in accordance with the present invention and the particular types of sensors 22 discussed are for illustration purposes only.

Two preferred types of ultrasonic sensors 22 that are utilized with the bayonet style locking system of the present invention are the airborne ultrasonic sensor 102, shown in FIGS. 9a, 9b, and 9c, and the contact ultrasonic sensor 104, shown in FIGS. 10a, 10b, 10c, and 10d. The preferred embodiments of both sensors 102 and 104 utilize piezoelectric transducers 25 to produce ultrasonic electrical signals that correspond to the ultrasonic sound waves reaching the sensors 102 and 104. The airborne sensor 102 preferably consist of a cylindrical housing 106 with a cylindrical PC board containing six contact pads 108 at one end that serves to establish electrical connections between the sensor 102 and the sensor socket 36. In addition, an identification circuit 23 and a piezoelectric transducer 25 are preferably located in the main body of the cylindrical housing 106. The piezoelectric transducer 25 is located behind a protective housing 110 in the end of the cylindrical housing 106 opposite the PC board containing the contact pads 108. The piezoelectric transducer 25 generates ultrasonic electrical signals in response to ultrasonic sound waves. The ultrasonic electrical signals are then split between two inputs on the cylindrical PC board containing the contact pads 108. The ultrasonic electrical signals are then sent from two of the contact pads on the cylindrical PC board 108 to the input of the received signal strength indicator 90 and the voltage controlled amplifier 76.

To allow the operator 20 to determine the precise location of small leaks or ultrasonic noise sources, a rubber cone 112 with a hole in the tip can be placed over the sensor 102 as shown in FIG. 11. The rubber cone diminishes the ability of the sensor 22 to detect ultrasonic sounds from anywhere but the open tip of the cone. Thus, the rubber cone 112 permits the operator 20 to more precisely locate a small leak. Materials other than rubber could be used to construct the cone 112, however, the rubber cone 112 does a particularly good job of isolating the ultrasonic sound waves and its flexibility makes it easy to use.

Because each sensor 22 contains identification information, variations in the airborne ultrasonic sensors 102 are easily accommodated by the ultrasonic monitoring system 10. New software can be installed in the ultrasonic monitoring system 10 that provides the system with the configuration information needed to accommodate the newly developed sensors 22.

The base of the contact sensor 104 is similar to the base of the airborne sensor 102. However, the receiving end of the contact sensor 104 consists of a long substantially hollow shaft 114. Ultrasonic vibrations are received by placing the tip hollow shaft 114 of the contact sensor 104 on the object that is suspected of radiating ultrasonic sound waves. To reinforce and stabilize the shaft 114 of the contact sensor 104, an adjustable washer 113, that is received by threads located on the cylindrical housing 106 at the base of the shaft 114, is tightened until the contact sensor 104 is firmly held in the sensor socket 36. A piezoelectric transducer 25 is located in the base of the shaft 114. Placing the tip of the shaft 114 against an object producing ultrasonic sound waves causes the piezoelectric transducer 25 of the contact sensor 104 to produce ultrasonic electrical signals. While the airborne ultrasonic sensor 102 is mechanically self-resonant, the contact sensor 104 is not. Therefore, the contact sensor 104 preferably contains an inductive and capacitive band pass resonant filter 27 that is preferably tuned to a frequency of 40 KHz. In a fashion similar to that of the airborne sensor 102, the ultrasonic electrical signal is then split and sent to the cylindrical shaped PC board containing the contact pads 108 that provide electrical contacts to the sensor socket contact pins 42.

The ultrasonic contact sensor 104 preferably contains a temperature sensor 116 coaxially mounted within the ultrasonic sensing shaft 114. The tip 117 of the temperature sensor 116 is constructed out of a material, such as copper, that rapidly conducts heat. A resistance type temperature detection circuit as shown in FIG. 10d is the preferred approach to determining the surface temperature of the object being monitored. A section of resistance temperature dependent (RTD) material 115 is in close contact with the heat conductive tip 117 of the temperature sensor 116. Thus, the heat conductive tip 117 acts as a conductor of heat between the surface of the object whose temperature is being measured and the RTD material 115. The resistance of an RTD material 115 varies relatively rapidly with a change in temperature. Thus, by measuring the resistance of the RTD material 115, a temperature measurement can be obtained. When the temperature sensor 116 is placed in contact with the surface for which a temperature reading is desired, the temperature of the tip 117 changes almost immediately to the temperature of the surface it is in contact with. The section of RTD material 115 is in close contact with the tip 117 and, thus, also rapidly changes temperature. In a preferred embodiment using copper for the heat conducting tip 117 and platinum as the RTD material 115, the temperature sensor 116 has a time constant response of less than 500 milliseconds.

A constant current is supplied to the RTD section of material 115 by the temperature sense circuit 92. As the temperature of the RTD section 115 of the temperature sensor 116 varies, so does the resistance of the RTD section 115. By supplying a constant current to the RTD material 115, a voltage potential is created across the material 115 that is proportional to the temperature of the sensor tip 117. As the temperature varies so does the resistance of the section of RTD 115 and, thus, the corresponding voltage potential also varies. By measuring the voltage potential across the section of RTD material 115 in the temperature sensor 116, the microprocessor 78 can determine the temperature of the tip 117 of the temperature sensor 116 and, thus, the surface temperature of the area in question.

Knowing the surface temperature of an enclosure containing bearings, gears, steam traps, valves, or other machinery provides an indication of the condition of the machinery. Temperature information is particularly useful when measurements are taken over time and compared. Many mechanical failures result in friction which, in turn, generates heat. Thus, a sudden increase in the surface temperature of a machine tends to indicate a new machinery defect is creating more friction and consequently more heat. A slow increase in surface temperature may indicate slowly progressing wear and tear in the machinery. As a further example of how surface temperature might be used to diagnose equipment failure, consider steam traps that are used to remove condensate from a steam line. Steam traps usually fail in one of two ways. First, they can fail open, meaning that they remove the condensate but allow steam to escape from the system. Second, they can fail closed, meaning that the pipes become blocked so that no condensate is removed. The temperature of the exhaust line of a steam trap which has failed open will be very high. Conversely, if the steam trap is blocked, the temperature of the downstream pipes will be much lower. Therefore, comparing the known temperature of a steam trap or machine when it is functioning properly to its present temperature can provide clues to the device's current condition.

Figure 12:
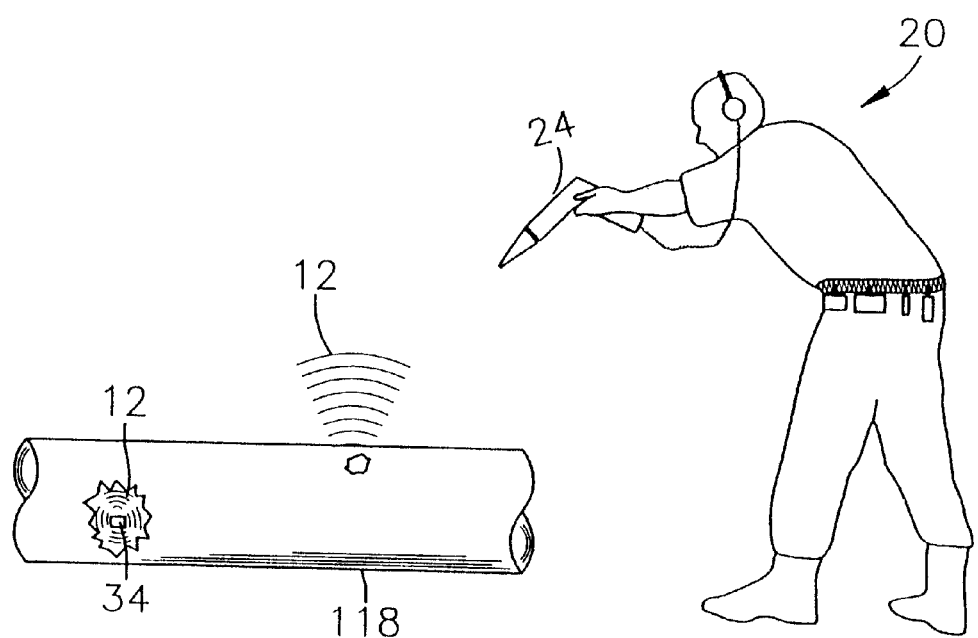
FIG. 12 is a pictorial representation of a method for using the ultrasonic transmitter to locate a hole in a pipe.

The ultrasonic monitoring system 10 further includes an ultrasonic sound wave transmitter 34 that permits the ultrasonic monitoring system 10 to locate holes in containers that are not producing ultrasonic sound waves. The ultrasonic sound wave transmitter 34 is turned on and placed inside a pipe, tank, or other sealed environment that it is desired to check for leaks. For example, as shown in FIG. 12, the ultrasonic sound wave transmitter 34 can be placed in a sealed environment 118. Once the ultrasonic sound wave transmitter 34 is activated, the operator 20 of the ultrasonic monitoring system 10 can use the ultrasonic sensor 22 in the elongate housing 24 to detect any ultrasonic sound waves 12 being emitted from the ultrasonic sound wave transmitter 34 that are escaping the sealed environment 118.

One of the primary benefits of using a digitally based ultrasonic monitoring system 10 that produces referenced decibel signal strength readings is the ability to store previously acquired data for later recall and analysis. Trending this digitally stored information allows the ultrasonic monitoring system 10 to detect changes in a machine's performance over time. For example, if the level of ultrasonic noise emitted by a particular machine dramatically increases from one week to another, it is highly likely that a machine defect has appeared or worsened in the previous week. In a similar vein, if a machine has consistently produced a large amount of ultrasonic noise over an extended period of time without malfunctioning, it is unlikely that another reading indicating the machine is producing a large amount of ultrasonic noise is indicative of a problem. Thus, much of the ultrasonic data acquired by the ultrasonic monitoring system 10 is primarily useful when compared to prior data collected under similar circumstances.

Temperature readings are also much more informative when trended over a period of time. For example, a surface temperature reading of 180 degrees Fahrenheit may not be particularly revealing in and of itself. However, a series of 120 degree Fahrenheit readings followed by a 180 degree reading is much more likely to be indicative of a problem. Thus, trending the data acquired by the ultrasonic monitoring system 10 dramatically improves the likelihood of detecting machinery defects.

Figure 13:
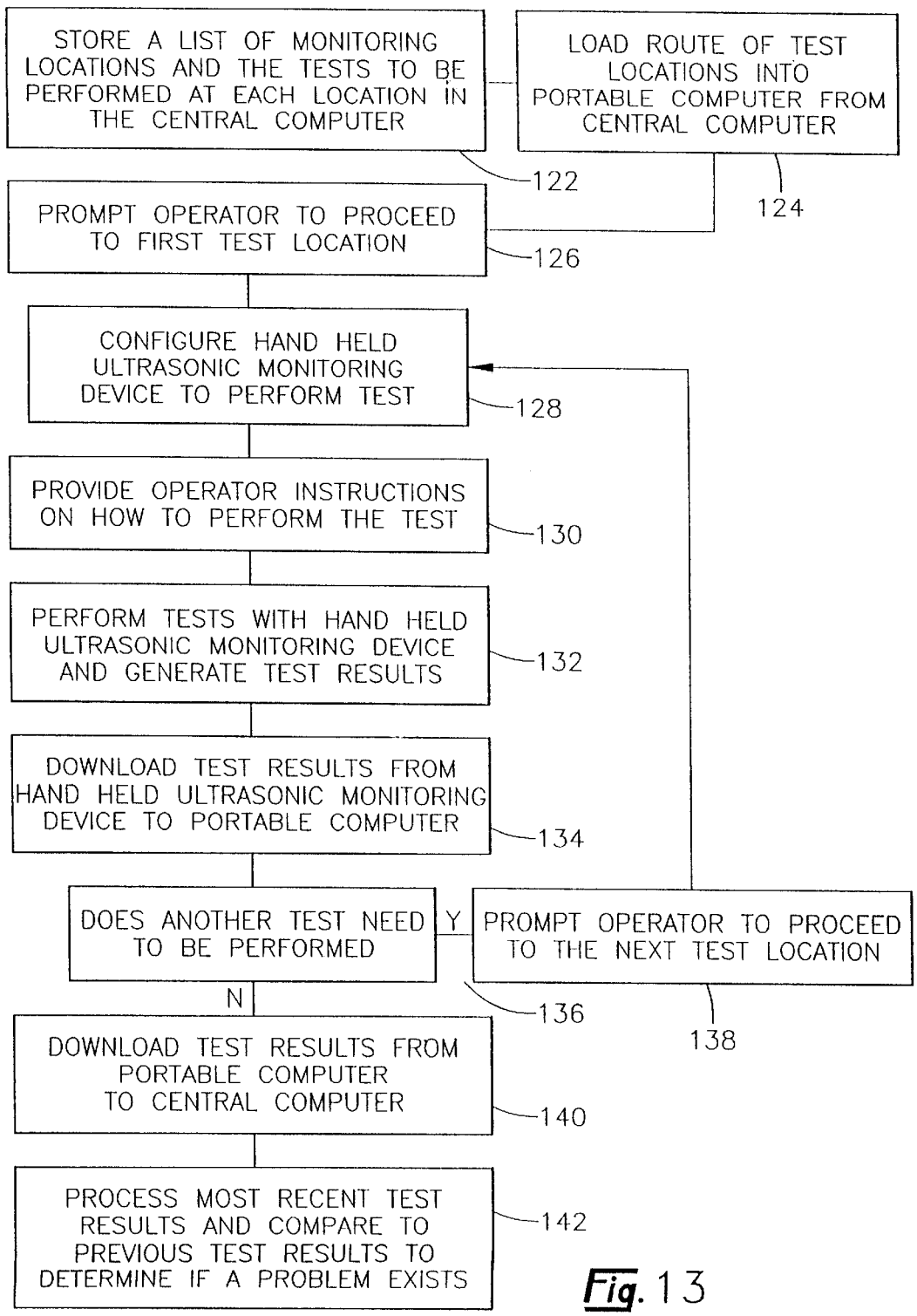
FIG. 13 is a flow chart outlining a route based method of monitoring equipment using the present invention.

As briefly mentioned before, the ultrasonic analysis system 10 preferably includes a microprocessor based portable personal computer. FIG. 13 is a flow chart showing the steps of a route based method of monitoring a series of machines with the ultrasonic monitoring system 10 of the present invention. The route based method uses a central processing and storage computer, a portable computer, and a hand held ultrasonic monitoring device. To set up a trendable ultrasonic monitoring system 10, a brief description of, and the location of, every machine that is to be monitored with the ultrasonic monitoring system 10 is entered into a central processing and storage computer. This step is shown in block 122 of FIG. 13. A monitoring schedule detailing the times at which each machine should be tested and the tests that should be performed on each machine is also programmed into the central processing computer. In a preferred embodiment, a ten character identification code is used to represent each machine and a three character identification code is used to represent each machine's location. When the time for testing the machines arrives, the central computer prompts the operator to download the testing information from the central computer to the portable computer, as shown in block 124. The portable computer examines the testing information and prompts the operator to proceed to the first testing location in block 126. The method then proceeds to block 128 wherein the portable computer loads the testing information needed for the first test into the hand held ultrasonic monitoring device. This testing information includes any configuration data needed for the particular tests to be performed on the machine. Furthermore, the alarm levels for the particular machine being tested are automatically sent from the portable computer to the hand held ultrasonic monitoring device. Thus, the portable computer prompts the operator to go to a particular location and perform a particular test on a particular machine and configures the microprocessor control unit in the hand held ultrasonic monitoring device to correctly perform the test. Furthermore, as shown in block 130, the portable computer provides a detailed description of how to perform the tests to the operator. It is important that the tests be performed in the same manner each time so that the results of the current test can be accurately compared to the results of previous tests. Once the ultrasonic sound wave and temperature measurements have been taken by the operator in block 132, the test results are downloaded from the hand held ultrasonic device to the portable computer in block 134.

In decisional block 136, the portable computer must determine whether another test needs to be performed. If another test needs to be performed, the portable computer prompts the operator to proceed to the next test location and the method returns to block 128. The software running on the portable computer is preferably flexible enough to auto increment through a predetermined monitoring route or receive external inputs, such as bar code information, which dictate the location in the manufacturing setting to be monitored. However, when all the required tests have been performed, the portable computer prompts the operator to download the test results from the portable computer to the central computer. In the final step of the method depicted in block 142, the central computer compares the test data from the most recent test to the data from previous tests to determine the condition of the machines being monitored.

The test results from previous measurements may be used to generate alarm levels for the next series of measurements. For example, an alarm level can be set so that if the ultrasonic noise level measurement from a particular machine is three decibels higher than the previous the ultrasonic noise level measurement an alarm is triggered. The increase in ultrasonic noise from one measurement to the next that is necessary to trigger an alarm may be varied by the operator depending upon the particular type of machine being monitored and the circumstances surrounding its monitoring. Similarly, the current test results may be automatically compared to predetermined criteria stored in memory to determine if an alarm situation exists. The predetermined criteria may be based upon historical or baseline data corresponding to past measurements taken from a particular type machine. In addition, even more complex criteria such as the expected ultrasonic sound wave production of a particular machine as a function of the amount of time the machine has been operating are easily accommodated by the route based system of the present invention.

Depending upon the memory requirements imposed by the number of devices being monitored and the number of tests being performed, the data contained in the portable computer may not need to be downloaded to a permanent base station. If the storage and processing capacity of a central computer is not required, the test data may be stored and analyzed by the portable computer. Furthermore, if sufficient memory exists in the hand held ultrasonic monitoring device, the hand held ultrasonic monitoring device can perform the steps necessary for a route based monitoring system.

Storing the ultrasonic electrical signals received from particular machines also improves the likelihood of detecting a machinery defect by listening to the heterodyned audio signals produced by the ultrasonic monitoring system 10. Before the operator of the ultrasonic monitoring system 10 listens to the current audio signals produced in response to the ultrasonic sound waves received from a particular machine, the operator can prompt the portable computer to playback the audio signals previously recorded from the particular machine. This makes it much easier for the operator of the ultrasonic monitoring system 10 to detect the small changes in the audio signals which are often indicative of a developing machinery defect.

The ultrasonic monitoring system 10 allows a user to input a number of conditions that will result in an alarm being generated. These alarms may be audible or visual depending on the user's preference. These alarms preferably include an alarm for exceeding a user-defined decibel level, an alarm for exceeding a user-defined temperature level, and an alarm to alert the user that the incoming signal is beginning to be clipped by the internal electronic circuitry in the elongate housing 24.

The decibel alarm is defined by accessing the alarm function with the mode input key 72 on the elongate housing 24 and using the up 70 and down 68 arrow input keys to set an alarm limit. Preferably, when the alarm level is reached, an audible alarm is heard in the headphones 26 and the referenced decibel readout on the display 66 flashes. The alarm limit may be triggered differently depending on which operating mode is selected. For example, in the instantaneous, peak hold and peak factor modes, the decibel alarm is preferably activated the first time the incoming signal reaches the user defined limit. However, when in the average mode, the decibel alarm is activated the first time the average reading reaches the user-defined limit.

The temperature alarm is also defined by accessing the temperature alarm function with the mode input key 72 and using the up 70 and down 68 and arrow keys to set the alarm limit. When the limit is reached, an audible alert is heard in the headphones 26 and the temperature readout on the display 66 flashes. The signal clipping alarm indicates the incoming signal is being clipped and that the user should decrease the volume. The signal clipping alarm can be either an audible alarm in the headphones 26 or a visual alarm on the display 66.

While the invention has been described in detail, it is to be expressly understood that it will be apparent to persons skilled in the relevant art that the invention may be modified without departing from the spirit of the invention. Various changes of form, design or arrangement may be made to the invention without departing from the spirit and scope of the invention. Therefore, the above mentioned description is to be considered exemplary, rather than limiting, and the true scope of the invention is that defined in the following claims.

What is claimed is:

1. A portable digital ultrasonic sound detection and analysis device for measuring and detecting ultrasonic sounds, the digital ultrasonic device comprising:

an elongate housing for enclosing the digital ultrasonic device wherein the elongate housing further comprises a grip that is designed to provide a handle that allows a user to carry and point the digital ultrasonic device and a trigger which is used to control the functioning of the digital ultrasonic device;

a set of sensors including at least a temperature sensor and an ultrasonic sensor;

a sensor socket located in the elongate housing of the ultrasonic device that is designed to interchangeably receive a sensor from the set of sensors wherein the sensor socket comprises:

a cavity having walls and a bottom portion for receiving the sensor from the set of sensors;

a set of pins located in the bottom portion of the sensor socket for providing electrical contacts between a plurality of electrical contacts on the sensor installed in the sensor socket and the digital ultrasonic device; and at least one groove located in the walls of the cavity wherein the at least one groove has an open receiving portion that begins at the rim of the cavity and extends a distance down the cavity walls to an ending position and a leg portion that extends substantially perpendicularly from the ending position of the open receiving portion;

at least one protrusion fixedly attached to the sides of each of the sensors in the set of sensors wherein the protrusion is shaped and positioned to be received in the at least one groove in a manner that removably secures the sensor in the sensor socket;

installation guide means which prevent a sensor from the set of sensors from being improperly installed in the sensor socket;

an identification circuit located on each sensor in the set of sensors that contains identification and configuration information concerning the sensor;

a power supply located in the grip of the elongate housing that provides a power supply voltage and a ground voltage to the digital ultrasonic device;

a received signal strength indicator for receiving ultrasonic electrical signals from a sensor installed in the sensor socket that correspond to ultrasonic sounds detected by the sensor and producing a signal indicative of the strength of the ultrasonic sounds;

a variable frequency sine wave oscillator for producing local oscillator frequency signals;

a mixer for receiving the ultrasonic electrical signals from a sensor installed in sensor socket and the local oscillator frequency signals from the variable frequency sine wave oscillator and heterodyning the ultrasonic electrical signals to produce audible frequency range signals that correspond to the ultrasonic electrical signals but are in the audible frequency range of a human being;

a pair of headphones that receive the audible frequency range signals and broadcast the audible frequency range signals so that they can be heard by a user of the digital ultrasonic device;

a temperature sense circuit for sending a constant current to an installed temperature sensor and creating a temperature signal corresponding to the temperature sensed by the installed sensor;

a set of input keys located on the elongate housing that allow the user to control the functioning of the digital ultrasonic device;

a display for displaying properties of the sensed ultrasonic electrical and temperature signals;

a microprocessor for controlling the functioning of the digital ultrasonic sound detection and analysis device;

a memory for selectably storing information concerning the ultrasonic electrical signals and configuration parameters for the set of sensors;

a communications port located on the elongate housing that allows the microprocessor in the digital ultrasonic device to communicate with a host computer;

a signal output for providing the signal indicative of the strength of the ultrasonic electrical signals received from the received signal strength indicator to an external machine analyzer for time domain and frequency analysis; and an ultrasonic tone generator for introducing an ultrasonic tone into a vessel, pipe or container that is being checked for holes or leaks.

2. A portable passive device for detecting and analyzing ultrasonic sound waves or vibrations, said portable device comprising:

an ultrasonic sensor for sensing ultrasonic sound or vibrations wherein said ultrasonic sensor produces ultrasonic electrical signals that correspond to the sensed ultrasonic sound or vibrations;

a sensor socket wherein said ultrasonic sensor may be interchangeably received in said sensor socket such that said ultrasonic sensor can be removed from said sensor socket and replaced by a second ultrasonic sensor wherein said second ultrasonic sensor senses different ultrasonic properties than said removed ultrasonic sensor;

digital processing means for receiving and digitally analyzing the ultrasonic electrical signals to produce a peak hold value of said ultrasonic electrical signals;

a memory for digitally storing results of said digital analysis; and output means for communicating the results of said digital analysis to a central computer.

3. The device of claim 2 wherein said ultrasonic sensor senses airborne ultrasonic sound and said second ultrasonic sensor senses ultrasonic vibrations by being placed into contact with an object producing ultrasonic vibrations.

4. The device of claim 3 wherein said output means further comprise an infrared communications port for sending and receiving data.

5. The device of claim 4 wherein the output means further comprise a display for visually displaying results of the digital analysis of the ultrasonic electrical signals and information concerning the functioning and configuration of the device.

6. The device of claim 5 further comprising a split signal path for providing said ultrasonic electrical signals to a received signal strength indicator circuit that produces a signal representative of the strength of the ultrasonic electrical signals and a frequency conversion means that produces audible frequency range signals that correspond to the ultrasonic electrical signals but are in the audible frequency range of a human being.

7. The device of claim 6 wherein the frequency conversion means is a heterodyne circuit.

8. The device of claim 7 wherein the digital processing means can be reprogrammed in the field to incorporate firmware updates.

9. The device of claim 8 wherein the device is powered by a rechargeable power supply.

10. The apparatus of claim 7 further comprising an ultrasonic sound wave generator that can be placed inside of an object so that ultrasonic sound waves will escape from any openings in the walls of the object.

11. The apparatus of claim 6 further comprising alarm means for indicating when the sensed ultrasonic electrical signals exceed a user selected threshold value.

12. The apparatus of claim 4 wherein either said first or said second ultrasonic sensor has an integral temperature sensor.

13. The apparatus of claim 4 wherein said received ultrasonic sensor is electrically connected to both a received signal strength indicator circuit and a heterodyning audio circuit by a split signal path when received in said sensor socket.

14. The device of claim 2 further comprising means for providing a referenced decibel value of the ultrasonic sound waves or ultrasonic vibrations to the output means.

15. The device of claim 14 further comprising an envelope detector for producing a demodulation envelope wherein a DC voltage value of an instantaneous point on said demodulation envelope corresponds to said referenced decibel value.

16. A passive apparatus for detecting and analyzing ultrasonic sound or vibrations wherein said apparatus is adapted to be portable, said apparatus comprising:

a first ultrasonic sensor for sensing ambient ultrasonic sound or vibrations and producing ultrasonic electrical signals that correspond to the ultrasonic sound or vibrations;

a second ultrasonic sensor for sensing ambient ultrasonic sound or vibrations and producing ultrasonic electrical signals that correspond to the ultrasonic sound or vibrations wherein said second ultrasonic sensor has sensing properties that are different from said first ultrasonic sensor; and a sensor socket for removably receiving either said first ultrasonic sensor or said second ultrasonic sensor and coupling said received ultrasonic sensor to a microprocessor wherein said microprocessor digitally analyzes said ultrasonic electrical signals by performing time domain analysis on said ultrasonic electrical signals.

17. An apparatus for detecting and analyzing ultrasonic sound or vibration, said apparatus comprising:

a pistol shaped housing for containing the apparatus wherein said pistol shaped housing is adapted to be portably held in the hand of a user;

a trigger mounted on said pistol shaped housing for controlling said apparatus;

a sensor socket on said pistol shaped housing for interchangeably receiving a sensing module from a set of sensing modules wherein said received sensing module senses ultrasonic sound or vibrations and produces electrical signals corresponding to said sensed ultrasonic sound or vibrations;

a microprocessor for receiving and analyzing said electrical signals and producing data including a peak hold value and a referenced decibel value;

an audio output circuit for producing a heterodyned audio output signal based on said electrical signals;

a memory for storing selected portions of said produced data;

an RS 232 data output port for outputting selected portions of said produced data such that said data can be trended;

a display for displaying said referenced decibel output; and a headphone output on said pistol shaped housing for receiving said heterodyned audio output signal and providing an audio output to a pair of headphones.

18. A portable passive device for detecting and analyzing ultrasonic sound waves or vibrations, said portable device comprising:

a sensor socket for interchangeably receiving an ultrasonic sensor from a set of ultrasonic sensors wherein said set of sensors includes a first ultrasonic sensor that senses airborne ultrasonic sound and a second ultrasonic sensor that senses ultrasonic vibrations by being placed into contact with an object producing ultrasonic vibrations;

digital processing means for receiving and digitally analyzing the ultrasonic electrical signals to produce a peak factor value, a peak hold value, an average signal level value or an instantaneous peak signal value of said ultrasonic electrical signals;

a memory for digitally storing results of said digital analysis; and output means for communicating the results of said digital analysis to a central computer.

* * * * *